(12) United States Patent
Bohnen

(10) Patent No.: US 6,417,302 B1
(45) Date of Patent: Jul. 9, 2002

(54) COMPOUNDS CONTAINING BORON AND ALUMINIUM

(75) Inventor: Hans Bohnen, Moers (DE)

(73) Assignee: BASELL Polyolefine GmbH, Kehl (DE)

(*) Notice: Subject to any disclaimer, the term of this patent is extended or adjusted under 35 U.S.C. 154(b) by 0 days.

(21) Appl. No.: 09/463,436

(22) PCT Filed: Jul. 23, 1998

(86) PCT No.: PCT/EP98/04628

§ 371 (c)(1),
(2), (4) Date: Jan. 27, 2000

(87) PCT Pub. No.: WO99/06414

PCT Pub. Date: Feb. 11, 1999

(30) Foreign Application Priority Data

Jul. 31, 1997 (DE) .......................... 197 33 017

(51) Int. Cl.⁷ .................................. C08F 4/42
(52) U.S. Cl. ................ 526/160; 526/178; 526/151; 526/348; 526/943; 502/132; 502/202; 502/117; 502/102; 502/103
(58) Field of Search ................ 526/160, 943, 526/348, 151, 178; 502/132, 202, 117, 102, 103

(56) References Cited

U.S. PATENT DOCUMENTS

| 5,449,650 A | * | 9/1995 | Sugano et al. ............... 502/117 |
| 5,910,463 A | * | 6/1999 | Ernst et al. .................. 502/107 |
| 6,100,353 A | * | 8/2000 | Lynch et al. ................. 526/160 |

FOREIGN PATENT DOCUMENTS

| EP | 427 697 | 5/1991 |
| EP | 520 732 | 12/1992 |
| EP | 601 830 | 6/1994 |
| JP | 8 134123 A | * 5/1996 |
| WO | 95/14024 | 5/1995 |

OTHER PUBLICATIONS

Angew.Chem 1995, 107, 1255–1283–Brintzinger et al.
Chem.Ber. 117,863–874(2984) Anton et al.
Chem. Abs. vol. 126, No. 14, 1997.
J.Am. Chem.Soc. 1991, 113, 3623–3625, Yang et al.
Chem. Abstr. vol. 108 No. 15.
J.Org. Chem. 284 (1985) 1–4, Synoradzki et al.

* cited by examiner

Primary Examiner—David W. Wu
Assistant Examiner—Ling-Siu Choi
(74) Attorney, Agent, or Firm—Keil & Weinkauf

(57) ABSTRACT

The present invention relates to a chemical compound of the formula A

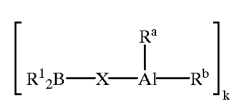

The compound can be employed as a catalyst component for the polymerization of olefins.

20 Claims, No Drawings

COMPOUNDS CONTAINING BORON AND ALUMINIUM

The present invention relates to a chemical compound which, in combination with a metallocene, can form a catalyst system which can advantageously be employed for the polymerization of olefins. The use of an aluminoxane, such as methylaluminoxane (MAO), as cocatalyst is unnecessary in this polymerization, and yet high catalyst activity is still achieved.

The role of cationic complexes in Ziegler-Natta polymerization using metallocenes is generally recognized (H. H. Brintzinger, D. Fischer, R. Mülhaupt, R. Rieger, R. Waymouth, Angew. Chem. 1995, 107, 1255–1283). As the most effective cocatalyst hitherto, MAO has the disadvantage of being employed in a large excess, which results in a high aluminum content in the polymer. The preparation of cationic alkyl complexes gives access to MAO-free catalysts of comparable activity, where the cocatalyst can be employed in a virtually stoichiometric amount.

The synthesis of "cation-similar" metallocene polymerization catalysts is described in J. Am. Chem. Soc. 1991, 113, 3623. This synthesis involves alkyl abstraction from an alkyl metallocene compound by means of trispentafluorophenylborane. EP 427 697 claims this synthetic principle and a corresponding catalyst system consisting of a neutral metallocene species (for example $CP_2ZrMe_2$), a Lewis acid (for example $B(C_6F_5)_3$) and alkylaluminum compounds. A process for the preparation of salts of the general form $LMX^+XA^-$ by the above-described principle is claimed in EP 520 732.

Disadvantages of known alternative cocatalyst systems are their high sensitivity to catalyst poisons and the problem of leaching on supporting of the catalyst systems.

The object of the present invention was to provide a chemical compound which avoids the disadvantages of the prior art and nevertheless facilitates high polymerization activities.

The present invention thus relates to a novel chemical compound and to a process for the preparation of this chemical compound. It furthermore relates to a catalyst system comprising at least one metallocene and at least one chemical compound according to the invention as cocatalyst. The catalyst system may additionally comprise further organometallic components and be immobilized on a support material. Furthermore, a process for the preparation of polyolefins is described.

The object is achieved by a chemical compound of the formula A

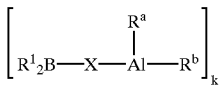

in which $R^1$ are identical or different and are a hydrogen atom, a halogen atom, a boron-free $C_1-C_{40}$-hydrocarbon-containing group, such as $C_1-C_{20}$-alkyl, $C_1-C_{20}$-haloalkyl, $C_1-C_{10}$-alkoxy, $C_6-C_{20}$-aryl, $C_6-C_{20}$-haloaryl, $C_6-C_{20}$-aryloxy, $C_7-C_{40}$-arylalkyl, $C_7-C_{40}$-haloarylalkyl, $C_7-C_{40}$-alkylaryl or $C_7-C_{40}$-haloalkylaryl, or $R^1$ can be an $OSiR^3_3$ group, in which $R^3$ are identical or different and are a hydrogen atom, a halogen atom, a $C_1-C_{40}$-hydrocarbon-containing group, such as $C_1-C_{20}$-alkyl, $C_1-C_{20}$-haloalkyl, $C_1-C_{10}$-alkoxy, $C_6-C_{20}$-aryl, $C_6-C_{20}$-haloaryl, $C_6-C_{20}$-aryloxy, $C_7-C_{40}$-arylalkyl, $C_7-C_{40}$-haloarylalkyl, $C_7-C_{40}$-alkylaryl or $C_7-C_{40}$-haloalkylaryl, or $R^1$ can be a $CH(SiR^4_3)_2$ group in which $R^4$ may be identical or different and are a hydrogen atom, a halogen atom, a $C_1-C_{40}$-hydrocarbon-containing group, such as $C_1-C_{20}$-alkyl, $C_1-C_{20}$-haloalkyl, $C_1-C_{10}$-alkoxy, $C_6-C_{20}$-aryl, $C_6-C_{20}$-haloaryl, $C_6-C_{20}$-aryloxy, $C_7-C_{40}$-arylalkyl, $C_7-C_{40}$-haloarylalkyl, $C_7-C_{40}$-alkylaryl or $C_7-C_{40}$-halo-alkylaryl, X is identical or different and is an element from group VIa of the Periodic Table of the Elements or is an NR group, where R is hydrogen or a $C_1-C_{20}$-hydrocarbon radical, such as $C_1-C_{20}$-alkyl or $C_1-C_{20}$-aryl, $R^a$ and $R^b$ may be identical or different and are a hydrogen atom, a halogen atom, a boron-free $C_1-C_{40}$-hydrocarbon-containing group, such as $C_1-C_{20}$-alkyl, $C_1-C_{20}$-haloalkyl, $C_1-C_{10}$-alkoxy, $C_6-C_{20}$-aryl, $C_6-C_{20}$-haloaryl, $C_6-C_{20}$-aryloxy, $C_7-C_{40}$-arylalkyl, $C_7-C_{40}$-haloarylalkyl, $C_7-C_{40}$-alkylaryl or $C_7-C_{40}$-haloalkylaryl, or $R^1$ can be an $OSiR^3_3$ group, in which $R^3$ are identical or different and are a hydrogen atom, a halogen atom, a $C_1-C_{40}$-hydrocarbon-containing group, such as $C_1-C_{20}$-alkyl, $C_1-C_{20}$-haloalkyl, $C_1-C_{10}$-alkoxy, $C_6-C_{20}$-aryl, $C_6-C_{20}$-haloaryl, $C_6-C_{20}$-aryloxy, $C_7-C_{40}$-arylalkyl, $C_7-C_{40}$-haloarylalkyl, $C_7-C_{40}$-alkylaryl or $C_7-C_{40}$-haloalkylaryl, In addition, $R^a$ and $R^b$ can be a boron-containing group, such as, for example, $-X-BR^1_2$, in which X is an element from group VIa of the Periodic Table of the Elements or an NR group, where R is hydrogen or a $C_1-C_{20}$-hydrocarbon radical, such as $C_1-C_{20}$-alkyl or $C_1-C_{20}$-aryl, and $R^1$ are identical or different and are a hydrogen atom, a halogen atom, a boron-free $C_1-C_{40}$-hydrocarbon-containing group, such as $C_1-C_{20}$-alkyl, $C_1-C_{20}$-haloalkyl, $C_1-C_{10}$-alkoxy, $C_6-C_{20}$-aryl, $C_6-C_{20}$-haloaryl, $C_6-C_{20}$-aryloxy, $C_7-C_{40}$-arylalkyl, $C_7-C_{40}$-haloarylalkyl, $C_7-C_{40}$-alkylaryl or $C_7-C_{40}$-haloalkylaryl, or $R^1$ can be an $OSiR^3_3$ group, in which $R^3$ are identical or different and are a hydrogen atom, a halogen atom, a $C_1-C_{40}$-hydrocarbon-containing group, such as $C_1-C_{20}$-alkyl, $C_1-C_{20}$-haloalkyl, $C_1-C_{10}$-alkoxy, $C_6-C_{20}$-aryl, $C_6-C_{20}$-haloaryl, $C_6-C_{20}$-aryloxy, $C_7-C_{40}$-arylalkyl, $C_7-C_{40}$-haloarylalkyl, $C_7-C_{40}$-alkylaryl or $C_7-C_{40}$-haloalkylaryl, or $R^1$ can be a $CH(SiR^4_3)_2$ group, in which $R^4$ are identical or different and are a hydrogen atom, a halogen atom, a $C_1-C_{40}$-hydrocarbon-containing group, such as $C_1-C_{20}$-alkyl, $C_1-C_{20}$-haloalkyl, $C_1-C_{10}$-alkoxy, $C_6-C_{20}$-aryl, $C_6-C_{20}$-haloaryl, $C_6-C_{20}$-aryloxy, $C_7-C_{40}$-arylalkyl, $C_7-C_{40}$-haloarylalkyl, $C_7-C_{40}$-alkylaryl or $C_7-C_{40}$-haloalkylaryl, and k is an integer from 1 to 100.

The compound of the formula A according to the invention can form dimers, trimers or higher oligomers through acid-base interactions, where k can be a natural number from 1 to 100.

Preferred chemical compounds of the formula A conform to the general formulae I, II and III:

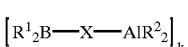

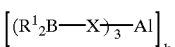

in which $R^1$ are identical or different and are a hydrogen atom, a halogen atom, a boron-free $C_1-C_{40}$-hydrocarbon-containing group, such as $C_1-C_{20}$-alkyl, $C_1-C_{20}$-haloalkyl, $C_1-C_{10}$-alkoxy, $C_6-C_{20}$-aryl, $C_6-C_{20}$-haloaryl, $C_6-C_{20}$- aryloxy, $C_7$–$C_{40}$-arylalkyl, $C_7$–$C_{40}$-haloarylalkyl, $C_7$–$C_{40}$-alkylaryl or $C_7$–$C_{40}$-haloalkylaryl, or $R^1$ can be an $OSiR^3_3$ group, in which $R^3$ are identical or different and are a hydrogen atom, a halogen atom, a $C_1$–$C_{40}$-hydrocarbon-containing group, such as $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl or $C_7$–$C_{40}$-haloalkylaryl, or $R^1$ can be a $CH(SiR^4_3)_2$ group in which $R^4$ may be identical or different and are a hydrogen atom, a halogen atom, a $C_1$–$C_{40}$-hydrocarbon-containing group, such as $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl or $C_7$–$C_{40}$-halo-lkylaryl, $R^2$ may be identical or different and are a hydrogen atom, a halogen atom, a boron-free $C_1$–$C_{40}$-hydrocarbon-containing group, such as $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl or $C_7$–$C_{40}$-haloalkylaryl, or $R^2$ can be an $OSiR^3_3$ group, in which $R^3$ are identical or different and are a hydrogen atom, a halogen atom, a $C_1$–$C_{40}$-hydrocarbon-containing group, such as $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-aryl-alkyl, $C_7$–$C_{40}$-haloarylalkyl, $C_7$–$C_{40}$-alkylaryl or $C_7$–$C_{40}$-haloalkylaryl.

X is identical or different and is an element from group VIa of the Periodic Table of the Elements or is an NR group, where R is hydrogen or a $C_1$–$C_{20}$-hydrocarbon radical, such as $C_1$–$C_{20}$-alkyl or $C_1$–$C_{20}$-aryl.

The compounds of the formulae I–III according to the invention can form dimers, trimers and higher oligomers with one another through acid-base interactions, where k can be an integer from 1 to 100.

Particular preference is given to compounds of the formulae I–III in which X is an oxygen atom or a NH group.

$R^1$ is preferably a boron-free $C_1$–$C_{40}$-hydrocarbon radical, which may be halogenated, preferably perhalogenated, by halogen, such as fluorine, chlorine, bromine or iodine, in particular a halogenated, preferably perhalogenated, $C_1$–$C_{30}$-alkyl group, such as trifluoromethyl, pentachloroethyl, heptafluoroisopropyl or monofluoroisobutyl, or a halogenated, preferably perhalogenated, $C_6$–$C_{30}$-aryl group, such as pentafluorophenyl, heptachloronaphthyl, heptafluoronaphthyl, heptafluorotolyl, 3,5-bis(trifluoromethyl)phenyl, 2,4,6-tris(trifluoromethyl)phenyl or 4-(trifluoromethyl)phenyl. $R^1$ can likewise preferably be radicals such as phenyl, methyl, ethyl, isopropyl, butyl, tolyl or 2,3-dimethylphenyl. Particular preference is given to the radicals pentafluorophenyl, phenyl, 3,5-bis(trifluoromethyl)phenyl and 4-methylphenyl.

$R^2$ is preferably a hydrogen atom or a boron-free $C_1$–$C_{40}$-hydrocarbon radical, which may be halogenated, preferably perhalogenated, by halogen, such as fluorine, chlorine, bromine or iodine, in particular a halogenated, preferably perhalogenated, $C_1$–$C_{30}$-alkyl group, such as trifluoromethyl, pentachloroethyl, heptafluoroisopropyl or monofluoroisobutyl, or a halogenated, preferably perhalogenated, $C_6$–$C_{30}$-aryl group, such as pentafluorophenyl, heptachloronaphthyl, heptafluoronaphthyl, heptafluorotolyl, 3,5-bis(trifluoromethyl)phenyl, 2,4,6-tris(trifluoromethyl)phenyl or 4-(trifluoromethyl)phenyl. $R^2$ can likewise preferably be radicals such as phenyl, methyl, ethyl, isopropyl, butyl, tolyl, -4-methyl phenyl or 2,3-dimethylphenyl. Particular preference is given to the radicals pentafluorophenyl, phenyl, 3,5-bis(trifluoromethyl)phenyl, 4-methylphenyl, methyl, ethyl, isopropyl, butyl and propyl. k is preferably an integer from 1 to 10, particularly preferably 1, 2, 3 or 4.

Compounds of the formula A are obtainable by reacting hydroxyorganoborines of the formula IV or diorganoborinic anhydrides of the formula V with organoaluminum compounds of the formula VI

in which $R^6$ is a hydrogen atom or a boron-free $C_1$–$C_{40}$-hydrocarbon-containing group, such as $C_1$–$C_{20}$-alkyl, $C_6$–$C_{20}$-aryl, $C_7$–$C_{40}$-arylalky or $C_7$–$C_{40}$-alkylaryl, and in which $R^1$ are identical or different and are a hydrogen atom, a halogen atom, a $C_1$–$C_{40}$-hydrocarbon-containing group, such as $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl or $C_7$–$C_{40}$-haloalkylaryl, or $R^1$ can be an $OSiR^3_3$ group, in which $R^3$ are identical or different and are a hydrogen atom, a halogen atom, a $C_1$–$C_{40}$-hydrocarbon-containing group, such as $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl or $C_7$–$C_{40}$-haloalkylaryl, or $R^1$ can be a $CH(SiR^4_3)_2$ group in which $R^4$ may be identical or different and are a hydrogen atom, a halogen atom, a $C_1$–$C_{40}$-hydrocarbon-containing group, such as $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl or $C_7$–$C_{40}$-halo-alkylaryl.

$R^1$ are identical or different and are preferably a boron-free $C_1$–$C_{40}$-hydrocarbon radical, which may be halogenated, preferably perhalogenated, by halogen, such as fluorine, chlorine, bromine or iodine, in particular a halogenated, preferably perhalogenated, $C_1$–$C_{30}$-alkyl group, such as trifluoromethyl, pentachloroethyl, heptafluoroisopropyl or monofluoroisobutyl, or a halogenated, preferably perhalogenated, $C_6$–$C_{30}$-aryl group, such as pentafluorophenyl, heptachloronaphthyl, heptafluoronaphthyl, heptafluorotolyl, 3,5-bis(trifluoromethyl)phenyl, 2,4,6-tris(trifluoromethyl)phenyl or 4-(trifluoromethyl)phenyl. $R^1$ can likewise preferably be radicals such as phenyl, biphenyl, naphthyl, anisyl, methyl, ethyl, isopropyl, butyl, tolyl or 2,3-dimethylphenyl. $R^2$ may be identical or different and are a hydrogen atom, a halogen atom, a boron-free $C_1$–$C_{40}$-hydrocarbon-containing group, such as $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl or $C_7$–$C_{40}$-haloalkylaryl, or $R^2$ can be an $OSiR^3_3$ group, in which $R^3$ are identical or different and are a hydrogen atom, a halogen atom, a $C_1$–$C_{40}$-hydrocarbon-containing group, such as $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-aryl-alkyl, $C_7$–$C_{40}$-haloarylalkyl, $C_7$–$C_{40}$-alkylaryl or $C_7$–$C_{40}$-haloalkylaryl.

$R^2$ is preferably a hydrogen atom, a halogen atom or a boron-free $C_1$–$C_{40}$-hydrocarbon radical, which may be halogenated, preferably perhalogenated, by halogen, such as fluorine, chlorine, bromine or iodine, in particular a halogenated, go preferably perhalogenated, $C_1$–$C_{30}$-alkyl group, such as trifluoromethyl, pentachloro-ethyl, heptafluoroisopropyl or monofluoroisobutyl, or a halogenated, preferably perhalogenated, $C_6$–$C_{30}$-aryl group, such as pentafluorophenyl, heptachloronaphthyl, heptafluoronaphthyl, heptafluorotolyl, 3,5-bis(trifluoromethyl)phenyl, 2,4,6-tris(trifluoromethyl)phenyl or 4-(trifluoromethyl)phenyl. $R^2$ can likewise preferably be radicals such as phenyl, methyl, ethyl, isopropyl, butyl, tolyl or 2,3-dimethylphenyl. X are identical or different and are an element from group VIa of the Periodic Table of the Elements or an NR group, in which R is a hydrogen atom or a $C_1$–$C_{20}$-hydrocarbon radical, such as $C_1$–$C_{20}$-alkyl or $C_1$–$C_{20}$-aryl, and n is an integer from 1 to 10. n is preferably 1, 2, 3 or 4. Preference is given to compounds in which X is an oxygen atom or an NH group.

Examples of compounds of the formulae IV and V are the following:
di(pentafluorophenyl)borinic acid
di(phenyl)borinic acid
di(o-tolyl)borinic acid
di(m-tolyl)borinic acid
di(p-tolyl)borinic acid
di(p-anisyl)borinic acid
di(p-biphenyl)borinic acid
di(p-chlorophenyl)borinic acid
di(α-naphthyl)borinic acid
di(ethyl)borinic acid
di(butyl)borinic acid
di(methyl)borinic acid
di(isopropyl)borinic acid
di(propyl)borinic acid
di(isobutyl)borinic acid
di(butyl)borinic acid
di(vinyl)borinic acid
dibis(trimethylsilyl)methylborinic acid
di(p-fluorophenyl)borinic acid
di(p-bromophenyl)borinic acid
di(mesityl)borinic acid
di(cyclohexyl)borinic acid
tert-butyl-phenylborinic acid
di(2-vinylphenyl)borinic acid
methylphenylborinic acid
ethyiphenylborinic acid
1-naphthylphenylborinic acid
di(cyclopentyl)borinic acid
di(ethyl)borinic anhydride
di(propyl)borinic anhydride
di(isopropyl)borinic anhydride
di(butyl)borinic anhydride
di(isobutyl)borinic anhydride
di(sec-butyl)borinic anhydride
di(allyl)borinic anhydride
di(methyl)borinic anhydride
di(phenyl)borinic anhydride
di(pentafluorophenyl)borinic anhydride
di(p-tolyl)borinic anhydride
di(1-naphthyl)borinic anhydride
di(mesityl)borinic anhydride
di(methylphenyl)borinic anhydride
di(3,5-bistrifluoromethylphenyl)borinic anhydride
diphenylboranylamine
dimethylboranylamine
dibutylboranylamine
diethylboranylamine
ethylmethylboranylamine
diisopropylboranylamine
diisopropylboranylamine
di-p-tolylboranylamine
dimesitylboranylamine
di-1-naphthylboranylamine
aminodibis(trimethylsilyl)methylborane Examples of compounds of the formula VI are the following:
trimethylaluminum
triethylaluminum
triisopropylaluminum
trihexylaluminum
trioctylaluminum
tri-n-butylaluminum
tri-n-propylaluminum
triisoprenealuminum
dimethylaluminum monochloride
diethylaluminum monochloride
diisobutylaluminum monochloride
methylaluminum sesquichloride
ethylaluminum sesquichloride
dimethylaluminum hydride
diethylaluminum hydride
diisopropylaluminum hydride
dimethylaluminum trimethylsiloxide
dimethylaluminum triethylsiloxide
phenylalane
pentafluorophenylalane
o-tolylalane For the preparation of the cocatalytic organoboron-aluminum compound of the formula A, one or more compounds of the formulae IV and V can be reacted with one or more compounds of the formula VI in any desired stoichiometric ratio, preferably in an amount of from 2 to 6 equivalents of a compound of the formula IV or V with one equivalent of the formula VI, particularly preferably in an amount of from 2 to 2.5 equivalents of a compound of the formula IV or V with one equivalent of the formula VI.

The reaction is carried out in an aliphatic or aromatic solvent, such as toluene, heptane, tetrahydrofuran or diethyl ether. It is also possible to use solvent mixtures. The cocatalytic organoboron-aluminum compounds of the formula A can be isolated or reacted further in solution without isolation. The term solution or solvent is also taken to mean a suspension or suspending medium, i.e. the starting materials employed in the process according to the invention and the products obtained can be partially or fully dissolved or partially or fully suspended.

Illustrative examples of the chemical compound of the formula A according to the invention are the following:

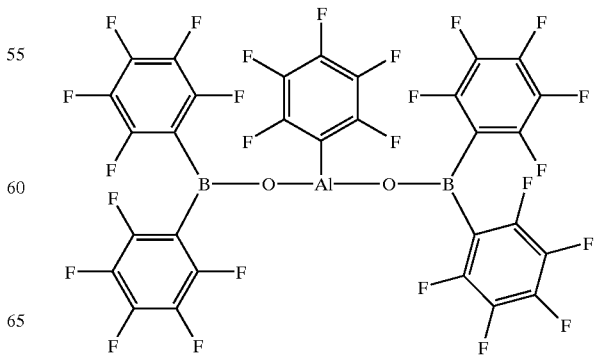

-continued
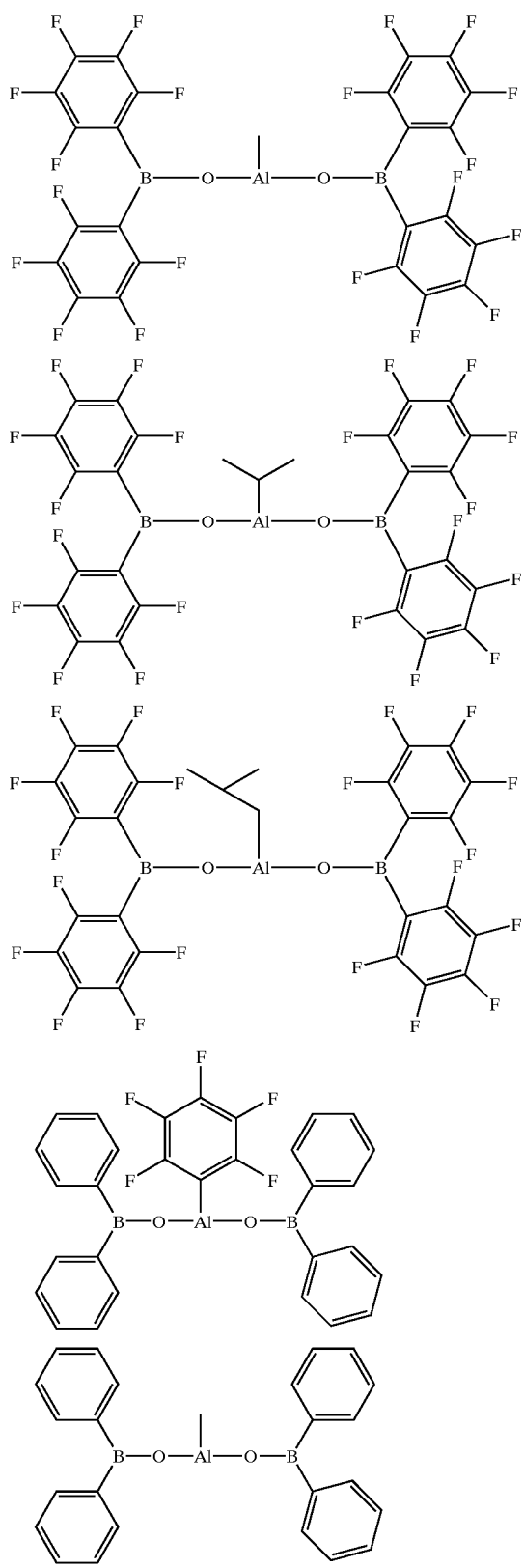
-continued
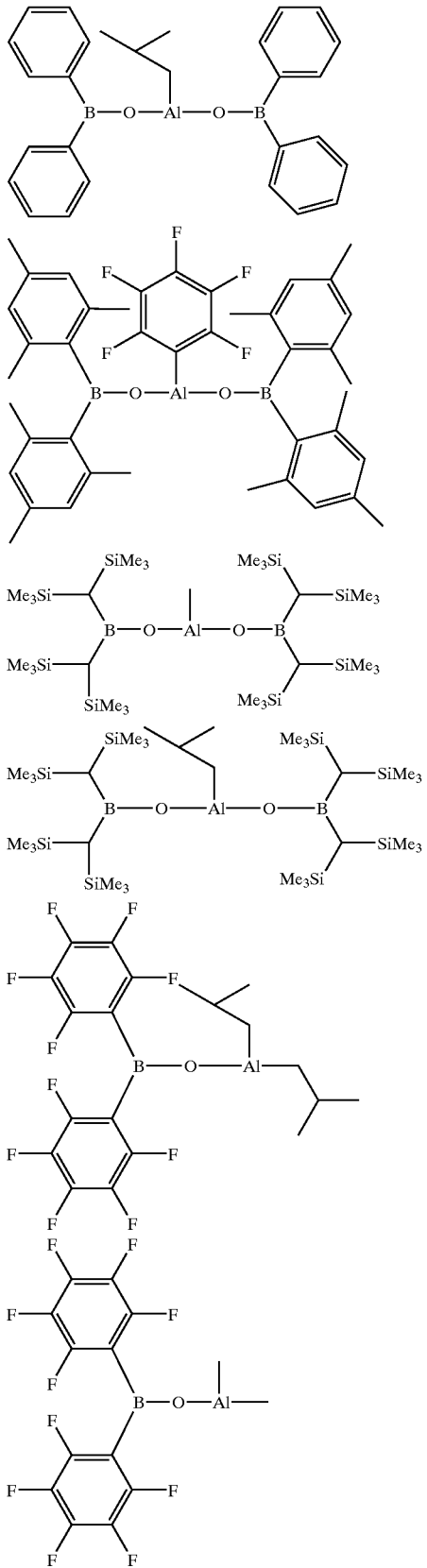

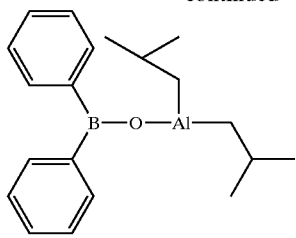

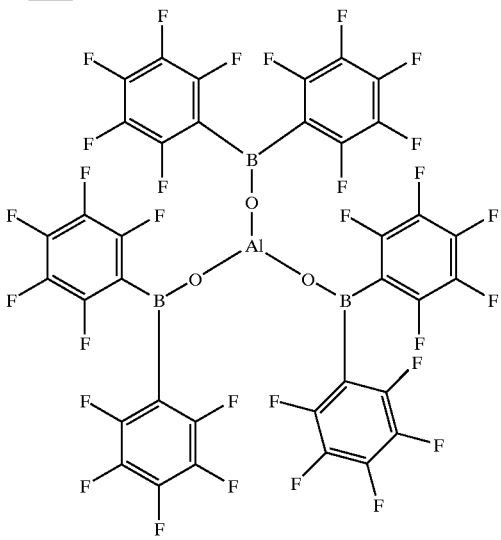

The chemical compound of the formula A according to the invention can be used together with a transition-metal compound as catalyst system, for example for the polymerization of olefins. The transition-metal compound employed is a metallocene compound. This can be, for example, a bridged or unbridged biscyclopentadienyl complex, as described, for example, in EP 129 368, EP 561 479, EP 545 304 and EP 576 970, monocyclopentadienyl complexes, such as bridged amidocyclopentadienyl complexes, which are described, for example, in EP 416 815, polycyclic pentadienyl complexes, as described in EP 632 063, tetrahydropentalenes substituted by π-ligands, as described in EP 659 758, or tetrahydroindenes substituted by π-ligands, as described in EP 661 300.

Preferred metallocene compounds are unbridged or bridged compounds of the formula VII

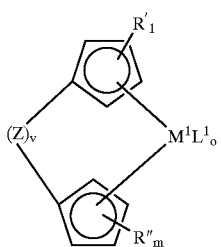

(VII)

in which

M$^1$ is a metal from sub-group III, IV, V or VI of the Periodic Table of the Elements, in particular Ti, Zr or Hf, R' are identical or different and are a hydrogen atom or SiR$^{3'}_3$, in which R$^{3'}$ are identical or different and are a hydrogen atom or a $C_1$–$C_{40}$-hydrocarbon-containing group, such as $C_1$–$C_{20}$-alkyl, $C_1$–$C_{10}$-fluoroalkyl, $C_1$–$C_{10}$-alkoxy, $C_6$–$C_{20}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or R' are a $C_1$–$C_{30}$-hydrocarbon-containing group, such as $C_1$–$C_{25}$-alkyl, for example methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, such as pyridyl, furyl or quinolyl, $C_7$–$C_{30}$-arylalkyl, $C_7$–$C_{30}$-alkylaryl, fluorine-containing $C_1$–$C_{25}$-alkyl, fluorine-containing $C_6$–$C_{24}$-aryl, fluorine-containing $C_7$–$C_{30}$-arylalkyl, fluorine-containing $C_7$–$C_{30}$-alkylaryl or $C_1$–$C_{12}$-alkoxy, or two or more radicals R' may be connected to one another in such a way that the radicals R' and the cyclopentadienyl ring atoms connecting them form a $C_4$–$C_{24}$-ring system, which may itself be substituted, R" are identical or different and are a hydrogen atom or SiR$^{3'}_3$, in which R$^{3'}$ are identical or different and are a hydrogen atom or a $C_1$–$C_{40}$-hydrocarbon-containing group, such as $C_1$–$C_{20}$-alkyl, $C_1$–$C_{10}$-fluoroalkyl, $C_1$–$C_{10}$-alkoxy, $C_6$–$C_{14}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or R" are a $C_1$–$C_{30}$-hydrocarbon-containing group, such as $C_1$–$C_{25}$-alkyl, for example methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, such as pyridyl, furyl or quinolyl, $C_7$–$C_{30}$-arylalkyl, $C_7$–$C_{30}$-alkylaryl, fluorine-containing $C_1$–$C_{25}$-alkyl, fluorine-containing $C_6$–$C_{24}$-aryl, fluorine-containing $C_7$–$C_{30}$-arylalkyl, fluorine-containing $C_7$–$C_{30}$-alkylaryl or $C_1$–$C_{12}$-alkoxy, or two or more radicals R" may be connected to one another in such a way that the radicals R" and the cyclopentadienyl ring atoms connecting them form a $C_4$–$C_{24}$-ring system, which may itself be substituted, l is 5 when v=0, and l is 4 when v=1, m is 5 when v=0, and m is 4 when v=1, L$^1$ may be identical or different and are a hydrogen atom, a halogen atom or a $C_1$–$C_{10}$-alkyl group, a $C_7$–$C_{40}$-arylalkyl group, a $C_6$–$C_{40}$-aryl group, or OR$^{6'}$, SR$^{6'}$, OSiR$^{6'}_3$, SiR$^{6'}_3$, PR$^{6'}_2$ or NR$^{6'}_2$, in which R$^{6'}$ is a halogen atom, a $C_1$–$C_{10}$-alkyl group, a halogenated $C_1$–$C_{10}$-alkyl group, a $C_6$–$C_{20}$-aryl group or a halogenated $C_6$–$C_{20}$-aryl group, or L$^1$ are a toluenesulfonyl, trifluoroacetyl, trifluoroacetoxyl, trifluoromethanesulfonyl, nonafluorobutanesulfonyl or 2,2,2-trifluoroethanesulfonyl group, o is an integer from 1 to 4, preferably 2, Z is a bridging structural unit between the two cyclopentadienyl rings, and v is 0 or 1.

Examples of Z are M$^2$R$^{5'}$R$^5$ groups, in which M$^2$ is carbon, silicon, germanium or tin, and R$^{5'}$ and R$^5$ are identical or different and are a $C_1$–$C_{20}$-hydrohydrocarbon-containing group, such as $C_1$–$C_{10}$-alkyl, $C_6$–$C_{14}$-aryl or trimethylsilyl. Z is preferably CH$_2$, CH$_2$CH$_2$, CH(CH$_3$)CH$_2$, CH(C$_4$H$_9$)C(CH$_3$)$_2$, C(CH$_3$)$_2$, (CH$_3$)$_2$Si, (CH$_3$)$_2$Ge, (CH$_3$)$_2$Sn, (C$_6$H$_5$)$_2$Si, (C$_6$H$_5$)(CH$_3$)Si, (C$_6$H$_5$)$_2$Ge, (C$_6$H$_5$)$_2$Sn, (CH$_2$)$_4$Si, CH$_2$Si(CH$_3$)$_2$, $_{o\text{-}C_6}$H$_4$ or 2,2'-(C$_6$H$_4$)$_2$. Z can also form a monocyclic or polycyclic ring system together with one or more radicals R' and/or R".

Preference is given to chiral, bridged metallocene compounds of the formula VII, in particular those in which v is 1 and one or two cyclopentadienyl rings are substituted in such a way that they form an indenyl ring. The indenyl ring is preferably substituted, in particular in the 2-, 4-, 2,4,5-, 2,4,6-, 2,4,7- or 2,4,5,6-position, by $C_1$–$C_{20}$-hydrocarbon-containing groups, such as $C_1$–$C_{10}$-alkyl or $C_6$–$C_{20}$-aryl, it also being possible for two or more substituents on the indenyl ring together to form a ring system.

Chiral, bridged metallocene compounds of the formula (VII) can be employed as pure racemic or pure meso compounds. However, it is also possible to use mixtures of a racemic compound and a meso compound.

Examples of metallocene compounds are the following:
dimethylsilanediylbis(indenyl)zirconium dichloride
dimethylsilanediylbis(4-naphthylindenyl)zirconium dichloride
dimethylsilanediylbis(2-methylbenzoindenyl)zirconium dichloride
dimethylsilanediylbis(2-methylindenyl)zirconium dichloride
dimethylsilanediylbis(2-methyl-4-(1-naphthyl)indenyl) zirconium dichloride
dimethylsilanediylbis(2-methyl-4-(2-naphthyl)indenyl) zirconium dichloride
dimethylsilanediylbis(2-methyl-4-phenylindenyl)zirconium dichloride
dimethylsilanediylbis(2-methyl-4-t-butylindenyl)zirconium dichloride
dimethylsilanediylbis(2-methyl-4-isopropylindenyl) zirconium dichloride
dimethylsilanediylbis(2-methyl-4-ethylindenyl)zirconium dichloride
dimethylsilanediylbis(2-methyl-acenaphthindenyl) zirconium dichloride
dimethylsilanediylbis(2,4-dimethylindenyl)zirconium dichloride
dimethylsilanediylbis(2-ethylindenyl)zirconium dichloride
dimethylsilanediylbis(2-ethyl-4-ethylindenyl)zirconium dichloride
dimethylsilanediylbis(2-ethyl-4-phenylindenyl)zirconium dichloride
dimethylsilanediylbis(2-methyl-4,5-benzoindenyl) zirconium dichloride
dimethylsilanediylbis(2-methyl-4,6-diisopropylindenyl) zirconium dichloride
dimethylsilanediylbis(2-methyl-4,5-diisopropylindenyl) zirconium dichloride
dimethylsilanediylbis(2,4,6-trimethylindenyl)zirconium dichloride
dimethylsilanediylbis(2,5,6-trimethylindenyl) zirconium dichloride
dimethylsilanediylbis(2,4,7-trimethylindenyl)zirconium dichloride
dimethylsilanediylbis(2-methyl-5-isobutylindenyl) zirconium dichloride
dimethylsilanediylbis(2-methyl-5-t-butylindenyl)zirconium dichloride
methyl(phenyl)silanediylbis(2-methyl-4-phenylindenyl) zirconium dichloride
methyl(phenyl)silanediylbis(2-methyl-5isobutylindenyl) zirconium dichloride
methyl(phenyl)silanediylbis(2-methyl-4-isopropylindenyl) zirconium dichloride
methyl(phenyl)silanediylbis(2-methyl-4,5-benzoindenyl) zirconium dichloride
methyl(phenyl)silanediylbis(2-methyl-4,5-(methylindenyl) zirconium dichloride
methyl(phenyl)silanediylbis(2-methyl-4,5-(tetramethylbenzo)indenyl)zirconium dichloride
methyl(phenyl)silanediylbis(2-methyl-4-acenaphthindenyl) zirconium dichloride
methyl(phenyl)silanediylbis(2-methylindenyl)zirconium dichloride
methyl(phenyl)silanediylbis(2-methyl-5-isobutylindenyl) zirconium dichloride
1,2-ethanediylbis(2-methyl-4-phenylindenyl)zirconium dichloride
1,4-butanediylbis(2-methyl-4-phenylindenyl)zirconium dichloride
1,2-ethanediylbis(2-methyl-4,6 diisopropylindenyl) zirconium dichloride
1,4-butanediylbis(2-methyl-4-isopropylindenyl)zirconium dichloride
1,4-butanediylbis(2-methyl-4,5-benzoindenyl)zirconium dichloride
1,2-ethanediylbis(2-methyl-4,5-benzoindenyl)zirconium dichloride
1,2-ethanediylbis(2,4,7-trimethylindenyl)zirconium dichloride
1,2-ethanediylbis(2-methylindenyl)zirconium dichloride
1,4-butanediylbis(2-methylindenyl)zirconium dichloride
[4-($\eta^5$-cyclopentadienyl)-4,6,6-trimethyl-($\eta^5$-4,5-tetrahydropentalene)]-dichlorozirconium
[4-($\eta^5$-3'-trimethylsilylcyclopentadienyl)-4,6,6-trimethyl-($\eta^5$-4,5-tetrahydropentalene)]dichlorozirconium
[4-($\eta^5$-3'-isopropyl-cyclopentadienyl)-4,6,6-trimethyl -($\eta^5$-4,5-tetrahydropentalene)]dichlorozirconium
[4-($\eta^5$-cyclopentadienyl)-4,7,7-trimethyl-($\eta^5$-4,5,6,7-tetrahydroindenyl)]-dichlorotitanium
[4-($\eta^5$-cyclopentadienyl)-4,7,7-trimethyl-($\eta^5$-4,5,6,7-tetrahydroindenyl)]-dichlorozirconium
[4-($\eta^5$-cyclopentadienyl)-4,7,7-trimethyl-($\eta^5$-4,5,6,7-tetrahydroindenyl)]-dichlorohafnium
[4-($\eta^5$-3'-tert-butylcyclopentadienyl)-4,7,7-trimethyl-($\eta^5$-4,5,6,7-tetrahydroindenyl)]dichlorotitanium
4-($\eta^5$-3'-isopropylcyclopentadienyl)-4,7,7-trimethyl-($\eta^5$-4,5,6,7-tetrahydroindenyl)]dichlorotitanium
4-($\eta^5$-3'-methylcyclopentadienyl)-4,7,7-trimethyl-($\eta^5$-4,5,6,7-tetrahydroindenyl)]dichlorotitanium
4-($\eta^5$-3'-trimethylsilylcyclopentadienyl)-2-trimethylsilyl-4,7,7-trimethyl-($\eta^5$-4,5,6,7-tetrahydroindenyl)] dichlorotitanium
4-($\eta^5$-3'-tert-butylcyclopentadienyl)-4,7,7-trimethyl-($\eta^5$-4,5,6,7-tetrahydroindenyl)]dichlorozirconium
(tertbutylamido)(tetramethyl-$\eta^5$-cyclopentadienyl) dimethylsilyl dichlorotitanium
(tertbutylamido)(tetramethyl-$\eta^5$-cyclopentadienyl)-1,2-ethanediyldichlorotitanium
(methylamido)(tetramethyl-$\eta^5$-cyclopentadienyl) dimethylsilyldichlorotitanium
(methylamido)(tetramethyl-$\eta^5$-cyclopentadienyl)-1,2-ethanediyldichlorotitanium
(tertbutylamido)(2,4-dimethyl-2,4-pentadien-1-yl) dimethylsilyldichlorotitanium
bis(cyclopentadienyl)zirconium dichloride
bis(n-butylcyclopentadienyl)zirconium dichloride
bis(1,3-dimethylcyclopentadienyl)zirconium dichloride
tetrachloro[1-[bis($\eta^5$-1H-inden-1-ylidene)methylsilyl]-3-$\eta^5$-cyclopenta- 2,4-dien-1-ylidene)-3-$\eta^5$-9H-fluoren-9-ylidene)butane]dizirconium
tetrachloro[2-[bis($\eta^5$-2-methyl-1H-inden-1-ylidene) methoxysilyl]-5-($\eta^5$-2,3,4,5-tetramethylcyclopenta-2,4-dien-1-ylidene)-5-($\eta^5$-9H-fluoren-9-ylidene)hexane] dizirconium
tetrachloro[1-[bis($\eta^5$-1H-inden-1-ylidene)methylsilyl]-6-($\eta^5$-cyclopenta-2,4-dien-1-ylidene)-6-($\eta^5$-9H-fluoren-9-ylidene)-3-oxaheptane]dizirconium dimethylsilanediylbis(indenyl)zirconiumdimethyl
dimethylsilanediylbis(4-naphthylindenyl)zirconiumdimethyl
dimethylsilanediylbis(2-methylbenzoindenyl)zirconiumdimethyl
dimethylsilanediylbis(2-methylindenyl)zirconiumdimethyl
dimethylsilanediylbis(2-methyl-4-(1-naphthyl)indenyl)zirconiumdimethyl
dimethylsilanediylbis(2-methyl-4-(2-naphthyl)indenyl)zirconiumdimethyl
dimethylsilanediylbis(2-methyl-4-phenylindenyl)zirconiumdimethyl
dimethylsilanediylbis(2-methyl-4-t-butylindenyl)zirconiumdimethyl
dimethylsilanediylbis(2-methyl-4-isopropylindenyl)zirconiumdimethyl
dimethylsilanediylbis(2-methyl-4-ethylindenyl)zirconiumdimethyl
dimethylsilanediylbis(2-methyl-4-acenaphthindenyl)zirconiumdimethyl
dimethylsilanediylbis(2,4-dimethylindenyl)zirconiumdimethyl
dimethylsilanediylbis(2-ethylindenyl)zirconiumdimethyl
dimethylsilanediylbis(2-ethyl-4-ethylindenyl)zirconiumdimethyl
dimethylsilanediylbis(2-ethyl-4-phenylindenyl)zirconiumdimethyl
dimethylsilanediylbis(2-methyl-4,5-benzoindenyl)zirconiumdimethyl
dimethylsilanediylbis(2-methyl-4,6 diisopropylindenyl)zirconiumdimethyl
dimethylsilanediylbis(2-methyl-4,5 diisopropylindenyl)zirconiumdimethyl
dimethylsilanediylbis(2,4,6-trimethylindenyl)zirconiumdimethyl
dimethylsilanediylbis(2,5,6-trimethylindenyl)zirconiumdimethyl
dimethylsilanediylbis(2,4,7-trimethylindenyl)zirconiumdimethyl
dimethylsilanediylbis(2-methyl-5-isobutylindenyl)zirconiumdimethyl
dimethylsilanediylbis(2-methyl-5-t-butylindenyl)zirconiumdimethyl
methyl(phenyl)silanediylbis(2-methyl-4-phenylindenyl)zirconiumdimethyl
methyl(phenyl)silanediylbis(2-methyl-4,6-diisopropylindenyl)zirconiumdimethyl
methyl(phenyl)silanediylbis(2-methyl-4-isopropylindenyl)zirconiumdimethyl
methyl(phenyl)silanediylbis(2-methyl-4,5-benzoindenyl)zirconiumdimethyl
methyl(phenyl)silanediylbis(2-methyl-4,5-(methylbenzo)indenyl)zirconiumdimethyl
methyl(phenyl)silanediylbis(2-methyl-4,5-(tetramethylbenzo)indenyl)-zirconiumdimethyl
methyl(phenyl)silanediylbis(2-methyl-4-acenaphthindenyl)zirconium-dimethyl
methyl(phenyl)silanediylbis(2-methylindenyl)zirconiumdimethyl
methyl(phenyl)silanediylbis(2-methyl-5-isobutylindenyl)zirconiumdimethyl
1,2-ethanediylbis(2-methyl-4-phenylindenyl)zirconiumdimethyl
1,4-butanediylbis(2-methyl-4-phenylindenyl)zirconiumdimethyl
1,2-ethanediylbis(2-methyl-4,6-diisopropylindenyl)zirconiumdimethyl
1,4-butanediylbis(2-methyl-4-isopropylindenyl)zirconiumdimethyl
1,4-butanediylbis(2-methyl-4,5-benzoindenyl)zirconiumdimethyl
1,2-ethanediylbis(2-methyl-4,5-benzoindenyl)zirconiumdimethyl
1,2-ethanediylbis(2,4,7-trimethylindenyl)zirconiumdimethyl
1,2-ethanediylbis(2-methylindenyl)zirconiumdimethyl
1,4-butanediylbis(2-methylindenyl)zirconiumdimethyl
[4-($\eta^5$-cyclopentadienyl)-4,6,6-trimethyl-($\eta^5$-4,5-tetrahydropentalene)]-dimethylzirconium
[4-($\eta^5$-3'-trimethylsilylcyclopentadienyl)-4,6,6-trimethyl-($\eta^5$-4,5-tetrahydropentalene)]dimethylzirconium
[4-($\eta^5$-3'-isopropylcyclopentadienyl)-4,6,6-trimethyl-($\eta^5$-4,5-tetrahydropentalene)]dimethylzirconium
[4-($\eta^5$-cyclopentadienyl)-4,7,7-trimethyl-($\eta^5$-4,5,6,7-tetrahydroindenyl)]-dimethyltitanium
[4-($\eta^5$-cyclopentadienyl)-4,7,7-trimethyl-($\eta^5$-4,5,6,7-tetrahydroindenyl)]-dimethylzirconium
[4-($\eta^5$-cyclopentadienyl)-4,7,7-trimethyl-($\eta^5$-4,5,6,7-tetrahydroindenyl)]-dimethylhafnium
[4-($\eta^5$-3'-tert-butyl-cyclopentadienyl)-4,7,7-trimethyl-($\eta^5$-4,5,6,7-tetrahydroindenyl)]dimethyltitanium
4-($\eta^5$-3'-isopropylcyclopentadienyl)-4,7,7-trimethyl-($\eta^5$-4,5,6,7-tetrahydroindenyl)]dimethyltitanium
dimethylsilanediylbis(2-methyl-4-(4'-tert-butylphenyl)indenyl)zirconium dichloride
dimethylsilanediylbis(2-methyl-4-(4'-tert-butylphenyl)indenyl)hafnuim dichloride
dimethylsilanediylbis(2-methyl-4-(4'-tert-butylphenyl)indenyl)titanium dichloride
dimethylsilanediylbis(2-methyl-4-(4'-methylphenyl)indenyl)zirconium dichloride
dimethylsilanediylbis(2-methyl-4-(4'-ethylphenyl)indenyl)zirconium dichloride
dimethylsilanediylbis(2-methyl-4-(4'-n-propylphenyl)indenyl)zirconium dichloride
dimethylsilanediylbis(2-methyl-4-(4'-isopropylphenyl)indenyl)zirconium dichloride
dimethylsilanediylbis(2-methyl-4-(4'-n-butylphenyl)indenyl)zirconium dichloride
dimethylsilanediylbis(2-methyl-4-(4'-hexylphenyl)indenyl)zirconium dichloride
dimethylsilanediylbis(2-methyl-4-(4'-sec-butylphenyl)indenyl)zirconium dichloride
dimethylsilanediylbis(2-ethyl-4-phenyl)indenyl)zirconium dichloride
dimethylsilanediylbis(2-ethyl-4-(4'-methylphenyl)indenyl)zirconium dichloride
dimethylsilanediylbis(2-ethyl-4-(4'-ethylphenyl)indenyl)zirconium dichloride
dimethylsilanediylbis(2-ethyl-4-(4'-n-propylphenyl)indenyl)zirconium dichloride
dimethylsilanediylbis(2-ethyl-4-(4'-isopropylphenyl)indenyl)zirconium dichloride
dimethylsilanediylbis(2-ethyl-4-(4'-n-butylphenyl)indenyl)zirconium dichloride
dimethylsilanediylbis(2-ethyl-4-(4'-hexylphenyl)indenyl)zirconium dichloride
dimethylsilanediylbis(2-ethyl-4-(4'-pentylphenyl)indenyl)zirconium dichloride
dimethylsilanediylbis(2-ethyl-4-(4'-cyclohexylphenyl)indenyl)zirconium dichloride
dimethylsilanediylbis(2-ethyl-4-(4'-sec-butylphenyl)indenyl)zirconium dichloride
dimethylsilanediylbis(2-ethyl-4-(4'-tert-butylphenyl)indenyl)zirconium dichloride dimethylsilanediylbis(2-n-propyl-4-phenyl)indenyl) zirconium dichloride
dimethylsilanediylbis(2-n-propyl-4-(4'-methylphenyl) indenyl)zirconium dichloride
dimethylsilanediylbis(2-n-propyl-4-(4'-ethylphenyl) indenyl)zirconium dichloride
dimethylsilanediylbis(2-n-propyl-4-(4'-n-propylphenyl) indenyl)zirconium dichloride
dimethylsilanediylbis(2-n-propyl-4-(4'-isopropylphenyl) indenyl)zirconium dichloride
dimethylsilanediylbis(2-n-propyl-4-(4'-n-butylphenyl) indenyl)zirconium dichloride
dimethylsilanediylbis(2-n-propyl-4-(4'-hexylphenyl) indenyl)zirconium dichloride
dimethylsilanediylbis(2-n-propyl-4-(4'-cyclohexylphenyl) indenyl)zirconium dichloride
dimethylsilanediylbis(2-n-propyl-4-(4'-sec-butylphenyl) indenyl)zirconium dichloride
dimethylsilanediylbis(2-n-propyl-4-(4'-tert-butylphenyl) indenyl)zirconium dichloride
dimethylsilanediylbis(2-n-butyl-4-phenyl)indenyl) zirconium dichloride
dimethylsilanediylbis(2-n-butyl-4-(4'-methylphenyl) indenyl)zirconium dichloride
dimethylsilanediylbis(2-n-butyl-4-(4'-ethylphenyl)indenyl) zirconium dichloride
dimethylsilanediylbis(2-n-butyl-4-(4'-n-propylphenyl) indenyl)zirconium dichloride
dimethylsilanediylbis(2-n-butyl-4-(4'-isopropylphenyl) indenyl)zirconium dichloride
dimethylsilanediylbis(2-n-butyl-4-(4'-n-butylphenyl) indenyl)zirconium dichloride
dimethylsilanediylbis(2-n-butyl-4-(4'-hexylphenyl)indenyl) zirconium dichloride
dimethylsilanediylbis(2-n-butyl-4-(4'-cyclohexylphenyl) indenyl)zirconium dichloride
dimethylsilanediylbis(2-n-butyl-4-(4'-sec-butylphenyl) indenyl)zirconium dichloride
dimethylsilanediylbis(2-n-butyl-4-(4'-tert-butylphenyl) indenyl)zirconium dichloride
dimethylsilanediylbis(2-hexyl-4-phenyl)indenyl)zirconium dichloride
dimethylsilanediylbis(2-hexyl-4-(4'-methylphenyl)indenyl) zirconium dichloride
dimethylsilanediylbis(2-hexyl-4-(4'-ethylphenyl)indenyl) zirconium dichloride
dimethylsilanediylbis(2-hexyl-4-(4'-n-propylphenyl) indenyl)zirconium dichloride
dimethylsilanediylbis(2hexyl-4(4'-isopropylphenyl) indenyl)zirconium dichloride
dimethylsilanediylbis(2-hexyl-4-(4'-n-butylphenyl)indenyl) zirconium dichloride
dimethylsilanediylbis(2-hexyl-4-(4'-hexylphenyl)indenyl) zirconium dichloride
dimethylsilanediylbis(2-hexyl-4-(4'-sec-butylphenyl) indenyl)zirconium dichloride
dimethylsilanediylbis(2-hexyl-4-(4'-tert-butylphenyl) indenyl)zirconium dichloride
dimethylsilanediylbis(2-methyl-4-(4'-tert-butylphenyl) indenyl)zirconium bis(dimethylamide)
dimethylsilanediylbis(2-ethyl-4-(4'-tert-butylphenyl) indenyl)zirconiumdibenzyl
dimethylsilanediylbis(2-methyl-4-(4'-tert-butylphenyl) indenyl)zirconiumdimethyl
dimethylgermandiylbis(2-ethyl-4-(4'-tert-butylphenyl) indenyl)zirconium dichloride
dimethylgermandiylbis(2-ethyl-4-(4'-tert-butylphenyl) indenyl)hafnium dichloride
dimethylgermandiylbis(2-propyl-4-(4'-tert-butylphenyl) indenyl)titanium dichloride
dimethylgermandiylbis(2-methyl-4-(4'-tert-butylphenyl) indenyl)zirconium dichloride
ethylidenebis(2-ethyl-4-phenyl)indenyl)zirconium dichloride
ethylidenebis(2-ethyl-4-(4'-tert-butylphenyl)indenyl) zirconium dichloride
ethylidenebis(2-n-propyl-4-(4'-tert-butylphenyl)indenyl) zirconium dichloride
ethylidenebis(2-n-butyl-4-(4'-tert-butylphenyl)indenyl) titanium dichloride
ethylidenebis(2-hexyl-4-(4'-tert-butylphenyl)indenyl) zirconiumdibenzyl
ethylidenebis(2-ethyl-4-(4'-tert-butylphenyl)indenyl) hafniumdibenzyl
ethylidenebis(2-methyl-4-(4'-tert-butylphenyl)indenyl) titaniumdibenzyl
ethylidenebis(2-methyl-4-(4'-tert-butylphenyl)indenyl) zirconium dichloride
ethylidenebis(2-ethyl-4-(4'-tert-butylphenyl)indenyl) hafniumdimethyl
ethylidenebis(2-n-propyl-4-phenyl)indenyl) titaniumdimethyl
ethylidenebis(2-ethyl-4-(4'-tert-butylphenyl)indenyl) zirconium bis(dimethylamide)
ethylidenebis(2-ethyl-4-(4'-tert-butylphenyl)indenyl) hafnium bis(dimethylamide)
ethylidenebis(2-ethyl-4-(4'-tert-butylphenyl)indenyl) titanium bis(dimethylamide)
methylethylidenebis(2-ethyl-4-(4'-tert-butylphenyl)indenyl) zirconium dichloride
methylethylidenebis(2ethyl-4-(4'-tert-butylphenyl)indenyl) hafnium dichloride
phenylphosphanediyl(2-ethyl-4-(4'-tert-butylphenyl) indenyl)zirconium dichloride
phenylphosphanediyl(2-methyl-4-(4'-tert-butylphenyl) indenyl)zirconium dichloride
phenylphosphanediyl(2-ethyl-4-(4'-tert-butylphenyl) indenyl)zirconium dichloride
dimethylsilanediyl(indenyl)zirconium dichloride
dimethylsilanediyl(4-naphthylindenyl)zirconium dichloride
dimethylsilanediyl(2-methylbenzoindenyl)zirconium dichloride
dimethylsilanediyl(2-methylindenyl)zirconium dichloride
dimethylsilanediyl(2-methyl-4-phenylindenyl)zirconium dichloride
dimethylsilanediyl(2-methyl-4-(1-naphthyl)indenyl) zirconium dichloride
dimethylsilanediyl(2-methyl-4-(2-naphthyl)indenyl) zirconium dichloride
dimethylsilanediyl(2-methyl-4-isopropylindenyl)zirconium dichloride
dimethylsilanediyl(2-methyl-4-acenaphthylindenyl) zirconium dichloride In order to prepare the catalyst system according to the invention, one or more compounds of the formula A can be reacted with a metallocene compound, for example of the formula VII, in any desired stoichiometric ratio. If desired, one or more compounds of the formula VI can additionally be added in any desired stoichiometric ratio.

In the preparation of the catalyst system according to the invention, preference is given to an Al:$M^1$ molar ratio between the compounds of the formula A and of the formula VII of from 0.01 to 100,000, particularly preferably from 0.1 to 1000, very particularly preferably from 1 to 100. To this end, a compound of the formula VI can additionally be added in an Al:M$^1$ molar ratio of from 0.01 to 10,000, preferably from 0.1 to 1000, very particularly preferably from 1 to 100.

The compounds can be brought into contact with one another in any possible sequence. A possible procedure is to dissolve or suspend an organotransition-metal compound of the formula VII in an aliphatic or aromatic solvent. An organoboron-aluminum compound of the formula A is then added either as such or in dissolved or suspended form. The reaction time is between 1 minute and 24 hours, preferably between 5 minutes and 120 minutes. The reaction temperature is between −10° C. and +200° C., preferably between 0° C. and 50° C. A compound of the formula VI in dissolved or suspended form is then added. The reaction time is between 1 minute and 24 hours, preferably between 5 minutes and 120 minutes. The reaction temperature is between −10° C. and +200° C., preferably between 0° C. and 50° C. The individual components can also be introduced into the polymerization reactor successively, in any desired sequence, or one or more compounds of the formulae IV and V react in a solvent with one or more compounds of the formula VI to give one or more compounds of the formula A. These are introduced into the polymerization reactor, and one or more compounds of the formula VI is then metered in.

The catalyst systems according to the invention can be employed for the polymerization in unsupported or supported form. The support preferably comprises at least one inorganic oxide, such as silicon oxide, aluminum oxide, zeolites, MgO, $ZrO_2$, $TiO_2$, $B_2O_3$, CaO, ZnO, $ThO_2$, $Na_2CO_3$, $K_2CO_3$, $CaCO_3$, $MgCO_3$, $Na_2SO_4$, $Al_2(SO_4)_3$, $BaSO_4$, $KNO_3$, $Mg(NO_3)_2$, $Al(NO_3)_3$, $Na_2O$, $K_2O$, or $Li_2O$, in particular silicon oxide and/or aluminum oxide. The support can also comprise at least one polymer, for example a homopolymer or copolymer, a crosslinked polymer or a polymer blend. Examples of polymers are polyethylene, polypropylene, polybutene, polystyrene, polystyrene crosslinked with divinylbenzene, polyvinyl chloride, acrylate-butadiene-styrene copolymer, polyamide, polymethacrylate, polycarbonate, polyester, polyacetal or polyvinyl alcohol.

The support can have a specific surface area in the range from 10 to 1000 m$^2$/g, preferably from 150 to 500 m$^2$/g. The mean particle size of the support can be from 1 to 500 μm, preferably from 5 to 350 μm, particularly preferably from 10 to 200 μm.

The support is preferably porous, with a pore volume of from 0.5 to 4.0 ml/g, preferably from 1.0 to 3.5 ml/g. A porous support has a certain proportion of cavities (pore volume). The shape of the pores is usually irregular, frequently spherical. The pores can be interconnected via small pore openings. The pore diameter is preferably from about 2 to 50 nm. The particle shape of the porous support can be irregular or spherical and can be modified by mechanical, chemical or thermal aftertreatment. The particle size of the support can be modified as desired by, for as example, cryogenic grinding and/or screening.

The support material may in addition have been pretreated with a compound of the formula VI. The compound of the formula VI can be the same as that used for the preparation of the catalyst system, but may also be different therefrom. In addition, the support material may have been pretreated with other chemical compounds, such as, for example, trimethylchlorosilane, tetrachlorosilane, amines, such as phenyldimethylamine, pyridine, mercaptans, such as mercaptopropylmethyldimethoxysilane, benzyl chloride, phenylmethyl chloride or tosylates.

The catalyst system according to the invention can be brought into contact with the support in any possible combination. One variant is to prepare the catalyst system in solution and then to react it with the support. To this end, an organometallic compound, for example of the formula VII, is initially introduced in an aliphatic or aromatic solvent, such as toluene, heptane, tetrahydrofuran or diethyl ether. One or more compounds of the formula A are subsequently added, either as such or in dissolved form. The reaction time is between 1 minute and 24 hours, preferably between 5 minutes and 120 minutes. The reaction temperature is between −10° C. and +200° C., preferably between 0° C. and 50° C. An organoaluminum compound of the formula VI, either as such or in dissolved or suspended form, is then added to the support. The reaction time is again between 1 minute and 24 hours, preferably between 5 minutes and 120 minutes. The reaction temperature is between −10° C. and +200° C., preferably between 0° C. and 50° C. All starting materials can be employed in any desired stoichiometric ratio. The Al:M$^1$ molar ratio between the compounds of the formula A and of the formula VII is preferably from 0.1 to 1000, very particularly from 1 to 100. To this end, a compound of the formula VII is preferably employed in a molar ratio of from 0.1 to 1000, very particularly preferably from 1 to 100. The supported catalyst system can be employed directly for the polymerization. However, it can also be employed for the polymerization in resuspended form after removal of the solvent.

In addition, a process for the preparation of an olefin polymer in the presence of the catalyst system according to the invention is described. The polymerization can be a homopolymerization or a copolymerization.

Preference is given to the polymerization of olefins of the formula R$^\alpha$—CH═CH—R$^\beta$, in which R$^\alpha$ and R$^\beta$ are identical or different and are a hydrogen atom, a halogen atom, an alkoxy, hydroxyl, alkylhydroxyl, aldehyde, carboxyl or carboxylate group or a saturated or unsaturated hydrocarbon radical having 1 to 20 carbon atoms, in particular 1 to 10 carbon atoms, which may be substituted by an alkoxy, hydroxyl, alkylhydroxyl, aldehyde, carboxyl or carboxylate group, or R$^\alpha$ and R$^\beta$, together with the atoms connecting them, form one or more rings. Examples of such olefins are 1-olefins, such as ethylene, propylene, 1-butene, 1-hexene, 4-methyl-1-pentene, 1-octene, styrene, cyclic olefins, such as norbornene, vinylnorbornene, tetracyclododecene, ethylidenenorbornene, dienes, such as 1,3-butadiene or 1,4-hexadiene, biscyclopentadiene or methyl methacrylate.

In particular, propylene or ethylene is homopolymerized, ethylene is copolymerized with one or more $C_3$–$C_{20}$-1-olefins, in particular propylene, and/or with one or more $C_4$–$C_{20}$-dienes, in particular 1,3-butadiene, or norbornene and ethylene are copolymerized.

The polymerization is preferably carried out at a temperature of from −60 to 300° C., particularly preferably from 30 to 250° C. The pressure is from 0.5 to 2500 bar, preferably from 2 to 1500 bar. The polymerization can be carried out continuously or batchwise, in one or more steps, in solution, in suspension, in the gas phase or in a supercritical medium.

The supported catalyst system can be resuspended as a powder or with adherent solvent and metered into the polymerization system as a suspension in an inert suspending medium.

The catalyst system according to the invention can be used to carry out a prepolymerization, preferably using the (or one of the) olefin(s) employed in the polymerization.

In order to prepare olefin polymers having a broad molecular weight distribution, preference is given to catalyst systems which contain two or more different transition-metal compounds, for example metallocenes.

In order to remove catalyst poisons present in the olefin, purification using an alkylaluminum compound, for example trimethylaluminum, triethylaluminum or triisobutylaluminum, is advantageous. This purification can be carried out either in the polymerization system itself, or the olefin is brought into contact with the Al compound before introduction into the polymerization system, and is then separated again.

As molecular weight regulator and/or in order to increase the activity, hydrogen is added if necessary. The overall pressure in the polymerization system is from 0.5 to 2500 bar, preferably from 2 to 1500 bar. The compound according to the invention is used here in a concentration, based on the transition metal, of, preferably from $10^{-3}$ to $10^{-8}$ mol, preferably from $10^{-4}$ to $10^{-7}$ mol, of transition metal per $dm^3$ of solvent or per $dm^3$ of reactor volume.

Suitable solvents for the preparation of both the supported chemical compound according to the invention and of the catalyst system according to the invention are aliphatic or aromatic solvents, such as, for example, hexane or toluene, ethereal solvents, such as, for example, tetrahydrofuran or diethyl ether, or halogenated hydrocarbons, such as, for example, methylene chloride, or halogenated aromatic hydrocarbons, such as, for example, o-dichlorobenzene.

Before addition of the catalyst system comprising at least one supported chemical compound according to the invention and at least one transition-metal compound (such as a metallocene), another alkylaluminum compound, such as, for example, trimethylaluminum, triethylaluminum, triisobutylaluminum, trioctylaluminum or isoprenylaluminum, can additionally be introduced into the reactor in order to render the polymerization system inert (for example to remove catalyst poisons present in the olefin). This additional compound is added to the polymerization system in a concentration of from 100 to 0.01 mmol of Al per kg of reactor contents. Preference is given to triisobutylaluminum and triethylaluminum in a concentration of from 10 to 0.1 mmol of Al per kg of reactor contents; this allows the molar Al:M ratio to be kept low in the synthesis of a supported catalyst system.

The examples below serve to illustrate the invention in greater detail.

General information: the compounds were prepared and handled in the absence of air and moisture under an argon blanket (Schlenk technique). All solvents required were rendered absolute before use by boiling for a number of hours over suitable desiccants followed by distillation under argon.

Bis(pentafluorophenyl)borinic acid (R. D. Chambers et al., J. Chem. Soc., 1965, 3933) and bis(phenyl)borinic acid (G. E. Coates, J G. Livingstone, J. Chem. Soc. 1961, 4909) were prepared as described in the literature.

1st EXAMPLE

Synthesis of di[bis(pentafluorophenylboroxy)] methylalane 5 ml of trimethylaluminum (2 M in toluene, 10 mmol) are introduced in 45 ml of toluene. 6.92 g (20 mmol) of bis(pentafluorophenyl)borinic acid in 50 ml of toluene are added dropwise to this solution over the course of 15 minutes at −40° C. The mixture is stirred at −40° C. for 1 hour and then at room temperature for a further hour. The slightly cloudy, pale yellow solution is filtered through a G4 frit, giving a clear, pale yellow solution (0.1 M, based on Al) of bis(pentafluorophenylboroxy)methylalane in toluene.

2nd EXAMPLE

Synthesis of di[bis(pentafluorophenylboroxy)]-methylalane 5 ml of trimethylaluminum (2 M in toluene, 10 mmol) are introduced in 45 ml of toluene. 3.32 g (20 mmol) of bis(phenyl)borinic acid in 50 ml of toluene are added dropwise to this solution over the course of 15 minutes at −40° C. The mixture is stirred at −40° C. for 1 hour and then at room temperature for a further hour. The slightly cloudy, pale yellow solution is filtered through a G4 frit, giving a clear, pale yellow solution (0.1 M, based on Al) of bis(phenylboroxy)methylalane in toluene.

3rd EXAMPLE

Synthesis of di[bis(pentafluorophenylboroxy)] isopropylalane 10 ml of triisopropylaluminum (1 M in toluene, 10 mmol) are introduced in 50 ml of toluene. 6.92 g (20 mmol) of bis(pentafluorophenyl)borinic acid in 50 ml of toluene are added dropwise to this solution over the course of 15 minutes at −40° C. The mixture is stirred at −40° C. for 1 hour and then at room temperature for a further hour. The clear solution (0.1 M, based on Al) of bis(pentafluorophenylboroxy)triisopropylalane can be employed directly for the polymerization.

4th EXAMPLE

Synthesis of di[bis(pentafluorophenylboroxy)]-isopropylalane 10 ml of triisopropylaluminum (1 M in toluene, 10 mmol) are introduced in 50 ml of toluene. 3.32 g (20 mmol) of bis(phenyl)borinic acid in 50 ml of toluene are added dropwise to this solution over the course of 15 minutes at −40° C. The mixture is stirred at −40° C. for 1 hour and then at room temperature for a further hour. The clear solution (0.1 M, based on Al) of bis(phenylboroxy)triisopropylalane can be employed directly for the polymerization.

5th EXAMPLE

Preparation of the Catalyst System 9 ml of the cocatalyst stock solution prepared in Example 1 are added to a solution of 53 mg (90 μmol) of dimethylsilanediylbis(2-methyl-4-phenylindenyl) zirconiumdimethyl in 10.75 ml of toluene. 0.25 ml of trimethylaluminum (2 M in toluene) are then injected, and the mixture is stirred at room temperature for a further hour. 0.5 ml of the stock solution prepared are employed for introduction into the polymerization system.

6th EXAMPLE

Polymerization

A 300 ml polymerization autoclave (Parr 4560) is charged with 150 ml of heptane under an argon atmosphere. 1.1 ml of TIBA (20%) are then metered in, and the mixture is stirred at 20° C. for 20 minutes. The reactor is then heated to 50° C., and 0.5 ml of the catalyst solution prepared under Example 5 are injected. Ethylene is then introduced to a pressure of 10 bar, and the polymerization is carried out for one hour at constant ethylene pressure, giving 10.6 g of polyethylene powder. The catalyst activity is 8.08 kg of PE/g of metallocene×h.

7th EXAMPLE

Preparation of the Catalyst System 10 g of $SiO_2$ (MS 3030, PQ company, dried at 600° C. in a stream of argon) are added in portions to a solution of 100 mg (0.229 mmol) of dimethylsilanediylbis(2-methylindenyl)zirconiumdimethyl in 25 ml of toluene and 22.9 ml of the cocatalyst stock solution prepared in Example 1. The mixture is stirred at room temperature for one hour, and the solvent is then removed to constant weight in an oil-pump vacuum. 1 g of the supported catalyst are resuspended in 30 ml of Exxol for introduction into the polymerization system.

8th EXAMPLE

Polymerization

In parallel, a dry 16 dm$^3$ reactor is flushed firstly with nitrogen and then with propylene and charged with 10 dm$^3$ of liquid propylene. 0.5 cm$^3$ of a 20% triisobutylaluminum solution in Varsol diluted with 30 cm$^3$ of Exxol is then introduced into the reactor, and the batch is stirred at 30° C. for 15 minutes. The catalyst suspension is then introduced into the reactor. The reaction mixture is heated to the polymerization temperature of 60° C. (4° C./min), and the polymerization system is held at 60° C. for 1 hour by cooling. The polymerization is terminated by venting the remaining propylene. The polymer is dried in a vacuum drying cabinet, giving 1.7 kg of polypropylene powder. The reactor has no deposits on the inside wall or stirrer. The catalyst activity is 174 kg of PP/g of metallocene×h.

What is claimed is:

1. A compound of formula A

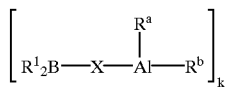

A wherein
- $R^1$ represents identical or different radicals selected from the group consisting of hydrogen, $C_1$–$C_{20}$-haloalkyl, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl, $C_7$–$C_{40}$-haloalkylaryl, $OSiR^3_3$ and $CH(SiR^4_3)_2$;
- X represents identical or different moieties selected from the group consisting of NR moieties and elements of group VIa of the Periodic Table of the Elements;
- $R^a$ and $R^b$ represent identical or different radicals selected from the group consisting of hydrogen, halogen, $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl, $C_7$–$C_{40}$-haloalkylaryl, $OSiR^3_3$ and $X$-$BR^1_2$;
- k is an integer from 1 to 100;
- $R^3$ represents identical or different radicals selected from the group consisting of hydrogen, halogen, $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl and $C_7$–$C_{40}$-haloalkylaryl;
- $R^4$ represents identical or different radicals selected from the group consisting of hydrogen, halogen, $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl and $C_7$–$C_{40}$-haloalkylaryl; and
- R is hydrogen, $C_1$–$C_{20}$-alkyl or $C_6$–$C_{20}$-aryl.

2. The compound of formula A defined in claim 1, which is obtained by reacting at least one compound of formula IV

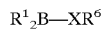

(IV)

wherein X is oxygen and $R^6$ is hydrogen, with a compound of formula VI

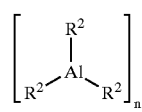

(VI)

wherein
- $R^2$ represents identical or different $C_1$–$C_{20}$-alkyl radicals, and
- n is 1, 2, 3 or 4.

3. The compound of formula A defined in claim 1, which is obtained by reacting bis(pentafluorophenyl)borinic acid or its anhydride with trimethylaluminum, triethylaluminum or with triisopropylaluminum.

4. A process for preparing the compound of formula A defined in claim 1, which comprises reacting at least one compound of formula IV or V

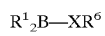

(IV)

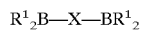

(V)

wherein $R^6$ is hydrogen, $C_1$–$C_{20}$-alkyl, $C_6$–$C_{20}$-aryl, $C_7$–$C_{40}$-arylalkyl or $C_7$–$C_{40}$-alkylaryl, with a compound of formula VI

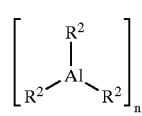

(VI)

wherein
- $R^2$ represents identical or different radicals selected from the group consisting of hydrogen, halogen, $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl, $C_7$–$C_{40}$-haloalkylaryl and $OSiR^3_3$; and
- n is an integer from 1 to 10.

5. The process of claim 4, wherein at least one compound of formula IV

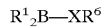

(IV)

wherein X is oxygen and $R^6$ is hydrogen, is reacted with a compound of formula VI

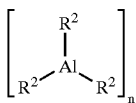
(VI)

wherein $R^2$ represents identical or different $C_1$–$C_{20}$-alkyl radicals, and n is 1, 2, 3 or 4.

6. The process of claim 4, wherein bis(pentafluorophenyl)-borinic acid is reacted with trimethylaluminum or with triisopropylaluminum.

7. A catalyst system comprising
   a) at least one compound of formula A defined in claim 1, and
   b) at least one metallocene compound, and optionally a support.

8. The catalyst system defined in claim 7, comprising at least one compound of formula A which is obtained by reacting at least one compound of formula IV

(IV)

wherein X is oxygen and $R^6$ is hydrogen, with a compound of formula VI

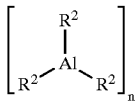
VI wherein $R^2$ represents identical or different $C_1$–$C_{20}$-alkyl radicals, and n is 1, 2, 3 or 4.

9. The catalyst system defined in claim 7, comprising at least one compound of formula A which is obtained by reacting bis(pentafluorophenyl)borinic acid or its anhydride with trimethylaluminum, triethylaluminum or with triisopropylaluminum.

10. The catalyst system defined in claim 7, which is obtained by bringing at least one compound of formula A into contact with at least one metallocene compound and optionally a support.

11. The catalyst system defined in claim 10, wherein at least one compound of formula A is obtained by reacting at least one compound of formula IV

(IV)

wherein X is oxygen and $R^6$ is hydrogen, with a compound of formula VI

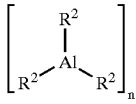
VI wherein $R^2$ represents identical or different $C_1$–$C_{20}$-alkyl radicals, and n is 1, 2, 3 or 4.

12. The catalyst system defined in claim 10, wherein at least one compound of formula A is obtained by reacting bis(pentafluorophenyl)borinic acid or its anhydride with trimethylaluminum, triethylaluminum or with triisopropylaluminum.

13. The catalyst system defined in claim 10, which is obtained by
   i) reacting at least one compound of formula IV or V

(IV)

(V)

wherein $R^6$ is hydrogen, $C_1$–$C_{20}$-alkyl, $C_6$–$C_{20}$-aryl, $C_7$–$C_{40}$-arylalkyl or $C_7$–$C_{40}$-alkylaryl, with a compound of formula VI

(VI)

wherein $R^2$ represents identical or different radicals selected from the group consisting of hydrogen, halogen, $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl, $C_7$–$C_{40}$-haloalkylaryl and $OSiR^3_3$; and n is an integer from 1 to 10, to obtain a reaction mixture comprising at least one compound of formula A, and ii) bringing the reaction mixture into contact with at least one metallocene compound and optionally a support.

14. The catalyst system defined in claim 13, wherein the reaction mixture is obtained by reacting at least one compound of formula IV

(IV)

wherein X is oxygen and $R^6$ is hydrogen, with a compound of formula VI

(VI)

wherein $R^2$ represents identical or different $C_1$–$C_{20}$-alkyl radicals, and n is 1, 2, 3 or 4.

15. The catalyst system defined in claim 13, wherein the reaction mixture is obtained by reacting bis(pentafluorophenyl)borinic acid or its anhydride with trimethylaluminum, triethylaluminum or with triisopropylaluminum.

16. A process for the manufacture of olefin homo- or copolymers, which comprises polymerizing identical or different olefins in the presence of a catalyst system comprising
   a) at least one compound of formula A as defined in claim 1, and
   b) at least one metallocene compound, and optionally a support.

17. The process of claim 16, wherein the catalyst system comprises at least one compound of formula A which is obtained by reacting at least one compound of formula IV $$R^1{}_2B\!-\!XR^6 \qquad (IV)$$

wherein X is oxygen and $R^6$ is hydrogen, with a compound of formula VI

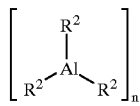

$$(VI)$$

wherein $R^2$ represents identical or different $C_1$–$C_{20}$-alkyl radicals, and n is 1, 2, 3 or 4.

18. The process of claim 16, wherein the catalyst system comprises at least one compound of formula A which is obtained by reacting bis(pentafluorophenyl)borinic acid or its anhydride with trimethylaluminum, triethylaluminum or with triisopropylaluminum.

19. The process of claim 16, wherein the catalyst system is obtained by bringing at least one compound of formula A into contact with at least one metallocene compound and optionally a support.

20. The process of claim 16, wherein the catalyst system is obtained by i) reacting at least one compound of formula IV or V $$R^1{}_2B\!-\!XR^6 \qquad (IV)$$

$$R^1{}_2B\!-\!X\!-\!BR^1{}_2 \qquad (V)$$

wherein $R^6$ is hydrogen, $C_1$–$C_{20}$-alkyl, $C_6$–$C_{20}$-aryl, $C_7$–$C_{40}$-arylalkyl or $C_7$–$C_{40}$-alkylaryl, with a compound of formula VI

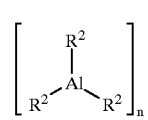

$$(VI)$$

wherein $R^2$ represents identical or different radicals selected from the group consisting of hydrogen, halogen, $C_1$–$C_{20}$-alkyl, $C_1$–$C_{20}$-haloalkyl, $C_1$–$C_{10}$-alkoxy, $C_6$–$C_{20}$-aryl, $C_6$–$C_{20}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl, $C_7$–$C_{40}$-haloalkylaryl and $OSiR^3{}_3$; and n is an integer from 1 to 10, to obtain a reaction mixture comprising at least one compound of formula A, and ii) bringing the reaction mixture into contact with at least one metallocene compound and optionally a support.

* * * * *